US007201879B2

(12) United States Patent
Hill et al.

(10) Patent No.: US 7,201,879 B2
(45) **Date of Patent: *Apr. 10, 2007**

(54) AEROSOL INTO LIQUID COLLECTOR FOR DEPOSITING PARTICLES FROM A LARGE VOLUME OF GAS INTO A SMALL VOLUME OF LIQUID

(75) Inventors: Steven Clyde Hill, Silver Spring, MD (US); Horn-Bond Lin, Fairfax, VA (US)

(73) Assignee: The United States of America as represented by the Secretary of the Army, Washington, DC (US)

( * ) Notice: Subject to any disclaimer, the term of this patent is extended or adjusted under 35 U.S.C. 154(b) by 144 days.

This patent is subject to a terminal disclaimer.

(21) Appl. No.: 10/997,094

(22) Filed: Nov. 19, 2004

(65) Prior Publication Data

US 2006/0110818 A1 May 25, 2006

(51) Int. Cl.

| | |
|---|---|
| *B32B 5/02* | (2006.01) |
| *B32B 27/04* | (2006.01) |
| *B32B 27/12* | (2006.01) |
| *G01N 30/96* | (2006.01) |
| *C12M 1/34* | (2006.01) |

(52) U.S. Cl. ........................ 422/88; 422/83; 422/82.05; 422/82.08; 435/7.1; 435/283.1; 435/288.7; 436/35; 436/36; 436/149; 436/153; 436/172; 436/181; 356/36; 356/37; 356/300; 356/318; 356/335; 250/281; 250/282; 250/283; 250/288; 250/299

(58) Field of Classification Search .................. 436/35, 436/36, 149, 153, 172, 181; 42/83, 88; 422/82.05, 422/82.08; 435/7.1, 283.1–283.2, 288.7; 356/36, 37, 300, 318, 335; 250/281–283, 250/288, 299

See application file for complete search history.

(56) References Cited

U.S. PATENT DOCUMENTS

2005/0214168 A1* 9/2005 Lin et al. ........................ 422/83

OTHER PUBLICATIONS

U.S. Appl. No. 10/708,1991, filed Feb. 2004, Hill.*

* cited by examiner

*Primary Examiner*—Long V. Le
*Assistant Examiner*—Jacqueline A. DiRamio
(74) *Attorney, Agent, or Firm*—A. David Spevack; Stephen Bloor

(57) ABSTRACT

An aerosol-into-liquid collector (ALC) for collecting gas-borne particles from a large volume of gas such as air into a small volume of liquid is described. The ALC uses a linear quadrupole to concentrate particles flowing in a gas and to help direct these concentrated particles toward a small volume of collection liquid so that these particles tend to combine with a small volume of collection liquid that can then be drawn from the ACL for further analysis. The particles in the gas are typically given a charge that is opposite to that of the charge imparted to the volume of collection liquid so that electrostatic forces help draw particles from the flowing gas into the small volume of liquid. The linear quadrupole focuses toward it axis particles that have the charge, mass and mobility to be stable in the linear quadrupole.

15 Claims, 4 Drawing Sheets

AEROSOL INTO LIQUID COLLECTOR FOR DEPOSITING PARTICLES FROM A LARGE VOLUME OF GAS INTO A SMALL VOLUME OF LIQUID

BACKGROUND OF THE INVENTION

1. Field of the Invention

This invention pertains generally to measurement of analyte in gas-borne particles, and particularly to collection of gas-borne particles into a liquid so that analytes in the particles can be analyzed.

2. Description of the Related Art

Devices are needed that can quickly detect and identify the presence of harmful materials in airborne particles. Airborne infectious agents such as bacteria and viruses can transmit diseases of humans, other animals, and plants. Some of these infectious agents, as well as some protein toxins have been used as biological-warfare (BW) agents. Some airborne proteins and pollens cause allergies. Also, improved methods for characterizing aerosols would be useful for understanding atmospheric chemistry, including the sources, chemical reactions, and fates of atmospheric particles. Here, "airborne particle" or "gas-borne particle" refers to both the solid particles and liquid droplets in an air or gas sample.

A group of particles in an air sample, of either indoor or outdoor air, may include many types of organic and inorganic materials and many types of bacterial and other biological materials. Individual particles may be homogenous or may be a complex mixture of materials. Identification of specific bacteria, viruses, or proteins, and many other types of complex chemicals that may be mixed in atmospheric particles requires first the collection of those particles so that they can be analyzed by appropriate techniques, e.g., immunoassay for bacteria, protein allergens, and other biological materials; culturing for bacteria and viruses; mass spectrometry for organic chemicals. For identification of specific bacteria or proteins using biochemical methods, the collection of these particles into a liquid is needed. For many types of analyses, e.g., single-particle infrared or Raman analysis, collection of airborne particles onto filters or other solid surfaces is desired, but that is not the interest in this invention.

One reason that there is a need for improved aerosol-into-liquid collectors is that there is a need for improved instruments which detect harmful biological aerosols, and which: (i) are sensitive to small numbers of particles in the air; (ii) are specific for whatever specific biomaterials the user desires to detect; (iii) provide a rapid response, with no more than a short delay between the time the analyte aerosol enters the instrument and the time the instrument indicates that an analyte has been identified; (iv) can run continuously; (v) has a low requirement for consumables; and (vi) has little need for operator time. If an aerosol into liquid collector, as part of an instrument to detect harmful aerosols, can collect the particles from a large volume of gas such as air into a small volume of liquid, then the overall instrument can be more sensitive and have a more rapid response, and if this instrument also does not loose a large amount of the collection liquid during the collection of the particles, it can have a lower requirement for consumables.

Investigators have worked for years to develop instruments for collecting aerosol particles into liquids. The literature describing different methods is large. Methods for collection of airborne particles, including methods for collection of particles into liquids, have been reviewed by M. L. Muilenberg, "Sampling Devices," Immunology and Allergy Clinics of North America, 23, 337–355 (2003). Liquid-impingement methods are widely used, but the volumes of liquid needed for microfluidic analyses are typically far smaller than are used with liquid impingers.

Some methods of collecting particles into a liquid are briefly summarized in the paper by I. Belostotski, V. V. Gridin, I. Schecter, and C. N. Yarnitzky, "Combined microdroplet and thin-film-assisted pre-concentration of lead traces for on-line monitoring using anodic striipping voltammetry," Analytical Bioanalytical Chemistry, 375, 482–488 (2003), especially in the introduction of that paper.

S. Zaromb, "High-Throughput Liquid-Absorption Air-Sampling Apparatus and Methods," U.S. Pat. No. 6,087,183, describes an apparatus to collect particles from air into liquid. In his apparatus 200 to 300 liters/min of air are drawing asymmetrically into a cylinder. This rapid flow of air swirling in the cylinder causes the liquid at the bottom of the cylinder to rise and also swirl inside the cylinder. Then particles from the air are collected into the liquid. The apparatus uses at least a few ml liquid per sample, and evaporation may be expected to be significant.

P. T. Call, V. M. Kenning, C. Call, J. G. Birmingham, and D. J. Hammerstrom, "Impact Particulate Collector Using a Rotary Impeller for Collecting Particulates and Moving a Fluid," U.S. Pat. No. 6,267,016 B1 (2001), describe another means to collect particles into a liquid. The airborne particles impact upon a rotating surface. A liquid is injected into the cavity that contains this rotating surface, and the particles may be washed into this liquid or may impact directly into the liquid.

P. J. Coyle, T. A. Pletcher, T. J. Davis, and S. Mangru, "Method and Apparatus for Concentrated Airborne Particle Collection," US Patent Application Publication, 2004/006907 A1, herein incorporated by reference, describe an apparatus to collect particles from a large volume of air into a relatively small volume of liquid in which a hydrophobic membrane establishes a "controllable air-fluid boundary" between a separation section where the particles are in air, and a capture section in which the particles are transported in liquid. A corona charger may be used to charge the aerosol so that the particles may be focused into the liquid stream.

I. A. Agranovski, V. Agranovski, S. A. Grinsphun, T. Reponen, and K. Willeke, "Collection of Airborne Microorganisms into Liquid by Bubbling through Porous Medium," Aerosol Science and Technology, 36, 502–509 (2002), describe a means to collect aerosols by bubbling them through a fibrous filter that is immersed in water. They demonstrate very efficient collection for an air sample of up to 4 liters/minute running for up to 8 hours.

D. A. Masquelier, F. P. Milanovich and K. Willeke, "High Air Volume to Low Liquid Volume Aerosol Collector," U.S. Pat. No. 6,520,034 B1, herein incorporated by reference, provide an apparatus to efficiently collect particles from a high volume (e.g., 225 Lpm) of air into a "collecting liquid having a volume not greater than about 100 to 300 microliters." They provide a means to reduce the loss of the collection liquid, which they need to reduce because they impinge the 225 liters/min of air onto this liquid in order for the particles in the air to be transferred to the liquid. This impinging of air into the liquid causes some of the liquid to form airborne droplets and some of the liquid to evaporate. They collect for re-use the liquid droplets, but not the evaporated liquid. The device is, small (typically 2 liters), lightweight (typically less than 1 Kg), and has low power requirements. The typical volume of liquid required per day is not stated.

V. V. Gridin, I. Litani-Barzilai, M. Kadosh, and I. Schecter, "A Renewable Liquid Droplet Method for On-Line Pollution Analysis by Multi-Photon Ionization," Analytical Chemistry, 69, 2098–2102 (1997), herein incorporated by reference, describe collection of gasses and aerosol particles into a pendant water droplet, where they are analyzed. The collection efficiency is not expected to be large, but would be sufficient for cases where particles that are in high concentration, and/or when the collection times are long.

V. Gartstein and A. D. Willey, "Dynamic Electrostatic Aerosol Collection Apparatus for Collection and Sampling Airborne Particulate Matter," US Patent Application Publication, 2004/0089156 A1, published May 13, 2004, describe a method of collection of aerosol particles by passing them through a spray of charged droplets that act as electrostatic collectors. The particles may be given a charge opposite to that of the droplets to enhance the collection efficiency. The liquid is re-circulated and is chosen to have a low volatility to reduce evaporative losses. The invention has similarities J. B. Fenn's, "Electrospray Air Sampler," US Patent Application Publication 2004/0023411 A1, published Feb. 5, 2004.

S. C. Hill, Aerosol Particle Analyzer for Measuring the Amount of Analyte in Airborne Particles, U.S. patent application Ser. No. 10/708,191, filed Feb. 14, 2004 and herein incorporated by reference, described a method for collecting particles into levitated droplets of an analysis liquid in order to rapidly detect analytes in the particles, and stated that the droplets of the analysis liquid could be collected and further analyzed. The use of a linear quadrupole to focus both the airborne particles and the airborne droplets of the analysis liquid to the axis of the linear quadrupole in order to increase the probability of collisions between particles and droplets is also described in that application. That invention was aimed specifically at the detection of analytes in particles without having the particles come into contact with any surface, so that there would be no problem of cross contamination from sample to sample. However, for detection of analytes or particles in cases where the tubing and instrumentation can be constructed so that the particles and analytes do not stick or cause cross contamination, the method is more complicated than required.

H. B. Lin and S. C. Hill, Aerosol Particle Analyzer for Measuring an Analyte in Airborne Particles, U.S. patent application Ser. No. 10/816579, filed Mar. 26, 2004, and herein incorporated by reference, described an apparatus for collection of particles into a small volume of an analysis liquid at the end of a capillary tube, where the rate of the collection of the particles is enhanced by electrostatic forces between the particles. The particles are given a charge that is opposite to that of the collection liquid at the end of the capillary tube. The goal was to measure the amount of an analyte in the particles, during the time shortly after the particles collide with and mix with the analysis liquid. However, it is stated that droplets of the analysis liquid with the combined particles could be stored for further analysis.

In summary, key prior art regarding collection of aerosol into a small volume of liquid provides for:
a) collection of particles into a flowing liquid that can be drawn directly into an analyzer, where aerodynamic forces are used to cause the particles to impact into the liquid (Gridin); because the gas moves slowly enough that it does not disrupt the slowly flowing liquid, the sampling rate and collection efficiency are relatively low;
b) collection of particles into a small volume of liquid using impaction of particles from a rapidly flowing gas (Willeke); because the gas flows rapidly, the sampling rate and collection efficiency can be large, the evaporation of the liquid into which the particles are collected can be relatively high, and the flow of the liquid is disrupted by the airflow;
c) collection of aerosol using a combination of virtual impaction, impaction, and electrostatic forces, and using a hydrophobic membrane (Coyle);
d) collection of particles using a spray of charged droplets (Fenn, Gartstein); if the liquid has a very low volatility to reduce the loss liquid, e.g., polyethers, as described by Gartstein, the particles would probably need to be removed from this liquid and responded in a aqueous solution before an antibody- or aptamer-based analysis could be accomplished;
e) collection of particles into a small droplet of a liquid that is either levitated or flowing in an air flow in a quadrupole (Hill, U.S. patent application Ser. No. 10/708,191).
f) collection of particles into a small volume of an collection liquid at the end of a capillary tube, where electrostatic forces provide the means to collect particles from the air without using such a high air flow that the liquid is disrupted and the liquid evaporates rapidly.

SUMMARY OF THE INVENTION

There is a need for improved aerosol-into-liquid collectors that collect the particles from a large volume of gas such as air into a small volume of liquid and that provides this small volume of liquid as an input to an instrument that can identify analytes in the particles or otherwise characterize the particles. The importance of this need is augmented by the progress being made in developing methods for sensitively measuring the amounts of analytes in very small sample volumes. For example, developments in microfluidic techniques and "lab-on-chip" techniques provide hope for the development of a continuously running aerosol identifier that may: (a) may be highly specific, (b) consume so little reagent for each analysis that it may be run essentially continuously, and (c) lend itself to an automated analysis.

An object of the present invention is to provide an improved aerosol-into-liquid collector (ALC) for depositing particles from a large-volume of gas into a small-volume of liquid, so that an instrument which analyzes this volume of liquid can be very sensitive to a small number of particles in the air, and so that, if the analyzer has a rapid response, the time to obtain the measured result can be short, so that there is only a short delay between the time the analyte aerosol enters the ALC and the time the analyzer instrument indicates that an analyte has been identified.

Another object of the present invention is to provide an ALC that has a low total requirement for liquid, not only a small final volume of liquid for each sample. This objective is not shared by some approaches to collection of particles into liquid, because for some applications the collection liquid may be as simple as pure water, and the instrument will be used in a place where water is readily available.

Yet another object of the present invention is to provide an ALC that can run continuously.

Yet another object of the present invention is to provide an ALC that provides the effluent particle-containing liquid in a precise location so that it can readily be taken into a analyzer that requires only a small sample volume.

In order to attain the objectives described above, according to an aspect of the present invention, there is provided an aerosol-into-liquid collector (ALC) that uses a linear quadrupole to concentrate particles flowing in a gas and to help direct these concentrated particles toward a small volume of collection liquid so that these particles tend to combine with the volume of collection liquid that can then be drawn from the ACL for further analysis. The particles in the gas are typically given a charge that is opposite to that of the charge imparted to the volume of collection liquid so that electrostatic forces draw particles from the flowing gas into the small volume of liquid.

The ALC is comprised of: (a) an aerosol particle handling subsystem further consisting of: (i) a substantially gas-tight container, (ii) a gas inlet, (iii) a linear quadrupole (LQ) consisting of four rods situated symmetrically around and parallel to a LQ axis having a first end of the LO axis and a second end of the LQ axis, that is positioned inside the gas-tight container such that the gas inlet is centered on an extension of the first end of the LQ axis, and the VCLO is centered on an extension of the second end of the LQ axis, (iv) a vacuum pump, and (v) at least one gas outlet that has a gas-tight connection to the vacuum pump, where the gas inlet, the LO, and the gas outlets are positioned such that when the vacuum pump generates a vacuum in the gas outlets, the gas that is drawn into the gas-tight container flows into the LO where at least some of the particles that have a combination of charge, mass, and mobility that is stable in the LQ, are focused toward the LQ axis, and are then drawn from the LQ substantially near the LQ axis so that the concentrated particles can be collected relatively efficiently, (b) a collection liquid (CL); (c) a means to generate and hold a volume of the collection liquid (VCL) within the path taken by particles that were focused by the LQ to positions near the LO axis and which exit the LO somewhat near the LO axis, so that these particles tend to combine with the VCL and so that the VCL that is exposed to the gas and particles becomes an exposed volume of collection liquid (EVCL); (d) a means to move the EVCL out of the gas-tight container through an output liquid port in the gas-tight container so that this EVCL can be analyzed by whatever instrumentation is connected to this output port.

The aforementioned features, objects, and advantages of this method over the prior art will become apparent to those skilled in the art from the following detailed description and accompanying drawings.

BRIEF DESCRIPTION OF THE DRAWINGS

In the drawings:

FIG. 1*a* is a schematic illustration of a side view of one embodiment of the ALC; in it the features of the charged volume of the collection liquid at the opening is drawn large for clarity;

FIG. 1*b* is a schematic illustration of an expanded side view of the collection liquid tubes, the wire electrode, the charged volume of the collection liquid, and the shield electrode.

FIG. 1*c* is a schematic illustration of the cross section of the collection liquid tubes, the wire electrode, and the shield electrode.

FIG. 2 is a schematic illustration of another embodiment of the ALC.

DETAILED DESCRIPTION OF THE PREFERRED EMBODIMENTS

Referring to FIG. 1*a*, FIG. 1*b*, and FIG. 1*c*, a preferred embodiment of an aerosol-into-liquid collector (ALC) 100 is immersed in a gas 120, such as the atmosphere, having particles 124 therein. Generally, the particles 124 are of many types. The particles 124 may be liquid, solid, or a mixture of liquid and solid. A collection liquid (CL) 480 is in a collection-liquid reservoir (CLR) 484.

The collection of the particles 124 into the CL 480 is accomplished as follows. A collection-liquid pump (CLP) 414 that is connected to the CLR 484 pumps the CL 480 into a proximal end of an incoming-section of the collection liquid tube (ICLT) 410. The ICLT 410 is part of a structure consisting of the ICLT 410 and a parallel outgoing Collection Liquid Tube (OCTL) 412, both with distal end openings, 430 and 432, respectfully. The distal ends of the ICLT 410 and OCLT 412 are aligned such that the openings 430 and 432 are in close proximity. A wire electrode 440 (illustrated in FIG. 1*b* and FIG. 1*c*), having a positive charge, is deployed within the ICLT 410. This imparts a positive charge to the CL 480 in the ICLT 410. The CLP 414 pumps the CL 480 through the ICLT 410 and out the opening 430 at the distal end of the ICLT 410. The CLP 414 pumps a predetermined amount of CL 480 into the ICLT 410, and this causes a like amount of positively charged CL 480 to exit the opening 430. This amount is chosen such that the positively charged CL 480 that exits the opening 430 is held to the distal ends of the ICLT 410 and OCLT 412, at the openings 430 and 432 by the surface tension inherent in the CL 480. This amount of positively charged CL 480 held by surface tension to the distal ends of the ICLT 410 and OCLT 412 is then a charged volume of the collection liquid at the openings (VCLO) 450.

A vacuum pump 192 creates a partial vacuum in a gas-tight container 140 and this partial vacuum then draws gas 120, and any particles 124 contained therein, through an induction port 126, a charger 250, and a gas inlet 142 connected, in order, with gas-tight means. The charger 250 imparts a negative charge to particles 124 contained in the gas 120 drawn into the gas-tight container 140.

A linear quadrupole (LQ) 500, consisting of four rods 506 situated symmetrically around and parallel to an LQ axis 510 having a first end of the LQ axis 512 and a second end of the LQ axis 514, is positioned inside the gas-tight container 140 such that the gas inlet 142 is centered on an extension of the first end of the LQ axis 512, and the VCLO 450 is centered on an extension of the second end of the LQ axis 514.

At least one gas outlet 144 is positioned in the gas-tight container 140 somewhat near an extension of the second end of the LQ axis 514 so that when the vacuum is generated by the pump 192, the gas 120 enters the gas-tight container 140 and flows in a direction substantially parallel to the LQ axis 510, past the VCLO 450, and then exits through the gas outlets 144, and gas outlet tubes 190 and vacuum pump 192, and then exhausts out of an exit port 128. As the gas flows through the LQ 500, particles 124 having a charge, mass, and mobility that allow them to be stable in this LQ 500 are focused by the LQ 500 and move toward the LQ axis 510. The particles 124 from in the gas 120 draw into the ALC 100 are moved into a volume near the LO axis 510 that is smaller than the volume of gas 120 drawn into the ALC 100, and are therefore concentrated by the LQ 500.

In a preferred embodiment the gas outlets 144 are positioned symmetrically around the LQ axis 510 so that as the flow of the gas 120 divides in order to move toward the gas outlets 144, the flow of the gas that crosses the LQ axis 510 is relatively small; therefore, the drag force, toward any one of the gas outlets 144, on particles 124 moving along the LQ axis 510 is relatively small.

As the gas 120 exits through the gas outlets 144, the particles 124 carried in this gas 120 and that have been concentrated near the LQ axis 510 are moving toward the VCLO 450 on or near the extension of the second end of the LQ axis 514. The momentum of the particles 124 moving toward the VCLO 450 helps increase the fraction of the particles 124 combining with the VCLO 450. In a preferred embodiment the axis of the LQ 510 is oriented vertically as in FIG. 1a, with the VCLO 450 down, so that gravitational forces also help direct the particles 124 toward the VCLO 450. This vertical orientation is more advantageous for collecting more massive particles 124.

In addition to the inertial and drag forces that may cause the particles 124 near the LQ axis to move toward the VCLO 450, the electrostatic force between the particles 124 that are negatively charged and the VCLO 450 that is positively charged draws the particles 124 toward the VCLO 450, and increases the fraction of the particles 124 that combine with the VCLO 450. An optional shield electrode 420 around the ICLT 410 and the OCLT 412, seen in FIG. 1b, is given a voltage that is opposite to that of the VCLO 450, and is of smaller magnitude than the voltage applied to the VCLO 450, so as to decrease the electrostatic attraction between the particles 124 and other parts of the ALC 100, so that the particles 124 are attracted primarily to the VCLO 450 itself.

After the VCLO 450 has been exposed to the gas 120 and to the charged particles 124 carried in the gas 120, so that those particles 124 may combine with it, it is termed an exposed volume of the collection liquid (EVCL) 456.

At the end of some preset time, an effluent pump 460 draws the EVCL 456 into the OCLT 412, through the opening 432 and then draws some of the gas 120 in the gas-tight container 140 into the OCLT 412. The effluent pump 460 pumps sufficiently hard to overcome the vacuum in the gas-tight container 140 created by the vacuum pump 192, and therefore does not allow the EVCL 456 to be drawn back into the gas-tight container 140. In some embodiments the surface tension alone will preclude the drawing of the EVCL 456 back into the gas-tight container 140. The effluent pump 460 continues to draw the EVCL 456 through the OCLT 412, and then pumps the EVCL 456 out through the effluent tube 462 so that the EVCL 456 can be analyzed by whatever instrumentation is desired. This EVCL 456 is the desired output of the ALC 100. Then the CLP 414 pumps more CL 480 into the ICLT 410 so that a new VCLO 450 is ready for the next measurement. This procedure allows the EVCL 456 to be analyzed without delay and without using more CL 480 than is needed. However, in other embodiments the CL 480 is continuously pumped into the VCLO 450, which is continually becoming the EVCL 456, and is continuously being pumped out through the effluent tube 462.

In embodiments that require long cycle times, and especially for cases where the solvent of the CL 480 tends to evaporate rapidly, because the temperature of the gas 120 is relatively large, and/or because there is a low partial pressure of the solvent of the CL 480 in the gas 120 drawn into the ALC 100, the CLP 414 may be required to replenish some of the CL 480 to maintain the VCLO 450.

In some embodiments, during the time that the particles 124 pass near and are attracted to the VCLO 450, the volume of the VCLO 450 extending from the opening 430 is kept relatively large, so that the total charge on the VCLO 450 can be kept relatively large, so that more of the negatively charged particles 124 are attracted to the VCLO 450 and collide with it, and so that more particles 124 collide with it because of their momentum and, in some cases, the gravitational forces on them.

In some embodiments the effluent pump 460 is also part of the instrument that analyzes the EVCL 456 after it has combined with particles 124.

In a simple embodiment, there is no effluent pump 460 or OCLT 412. In this embodiment the EVCL 456 is held on the ICLT 410 and when the preset exposure time has elapsed, the CLP 414 pumps more CL 480 into the ICLT 410, and the EVCL 456 is pushed from the ICLT 410 and falls because of gravity. In one embodiment the effluent tube 462 connects directly to the gas-tight container 140, and the EVCL 456 falls into the effluent tube 462 from which it can be drawn so that it can be further analyzed. In a similar embodiment, the effluent tube 462 has a sufficiently large diameter such that the EVCL 456 falls through the effluent tube 462.

The magnitude and frequency of the voltages that can be applied to the LQ 500, in order to focus particles 124 having different charges and masses toward the LQ axis 510 in cases where there are drag forces on the particles resulting from gas in a linear quadrupole, can be calculated as described by N. R. Whetten, "Macroscopic particle motion in quadrupole fields," Journal of Vacuum Science and Technology, 11, 515–518 (1974), especially p. 515, and are herein incorporated by reference. A more detailed derivation of the equations of motion, and a discussion of the solutions is described by Peter H. Dawson, Quadrupole Mass Spectrometry and Its Applications, (Elesevier, Amsterdam, 1976), especially equations 3.32 and 3.33, which apply to the case of a gas in the linear quadrupole that causes drag forces, and the rest of Chapter 3, pp. 65–77, herein incorporated by reference. For nonspherical particles the drag force on the particles depends upon the particle orientation, and so the analysis would be more complicated. However, for particles having dimensions on the order of a few micrometers, rotational diffusion times are relatively short. The trajectories of particles that satisfy the equations of motion in quadrupolar fields, where the drag forces on particles resulting from motion of particles relative to a gas, can be calculated using, for example, Runge-Kutta integration, as has been described by E. J. Davis, "Electrodynamic balance stability characteristics and applications to the study of aerocolloidal particles," Langmuir, 1, 379–384 (1985), herein incorporated by reference. Although the analysis by Davis is not identical to that of a linear quadrupole, the equations solved and their solutions are similar.

Examples of the use of linear quadrupoles to focus particles in air and keep them near the axis of the linear quadrupole axis are described by K. C. Ng, J. V. Ford, S. C. Jacobson, J. M. Ramsey, and M. D. Barnes, "Polymer microparticle arrays from electrodynamically focused microdroplet streams," Review of Scientific Instruments, 71, 2497–2499 (2000), herein incorporated by reference; by M. D. Barnes, N. Lermer, C.-Y. Kung, W. B. Whitten, J. M. Ramsey, S. C. Hill, "Real-time observation of single-molecule fluorescence in microdroplet streams," Optics Letters, 22, 1265–1267 (1997), herein incorporated by reference; and by C. Y. Kung, M. D. Barnes, N. Lermer, W. B. Whitten, J. M. Ramsey, "Confinement and manipulation of individual molecules in attoliter volumes," Analytical Chemistry, 70, 658–661 (1998), herein incorporated by reference, where particles as small as 1 micrometer diameter were shown to remain very near the LQ axis. Also, S. Arnold, P. Hendrie and B. V. Bronk, "Method and Apparatus for Suspending Microparticles," U.S. Pat. No. 5,532,140, herein incorporated by reference, described the use of a linear quadrupole with charged rings to control particle motion. A. F. Izmailov, A. S. Myerson, and S. Arnold, "A statistical understanding of nucleation," Journal of Crystal Growth, 196, 234–242 (1999), especially FIG. 1 and pages 238 and 240, both herein incorporated by reference, stated that their experiments show they "can simultaneously levitate in excess of 100 identical microdroplet particles within the same LQELT (linear quadrupole electrodynamic levitator trap). These particles produce a periodic one-dimensional lattice." In all of the examples mentioned above, particles were not collected from air, but droplets were generated with a droplet generator and injected into the linear quadrupole. The rods 506 of the LQ 500 may be cylindrical, but need not be.

The use of a linear quadrupole to focus airborne particles toward the axis of the linear quadrupole in order to increase the number of such particles that combine with an airborne charged-droplet-of-an-analysis-liquid that is also focused by the linear quadrupole, has been described as one of the embodiments in S. C. Hill, Aerosol Particle Analyzer for Measuring the Amount of Analyte in Airborne Particles, U.S. patent application Ser. No. 10/708,191, filed Feb. 14, 2004 and herein incorporated by reference. That application described a method for collecting particles into droplets of an analysis liquid for rapid analysis without contacting any surfaces, and stated that the droplets of the analysis liquid could be collected and further analyzed. The present application differs from Hill, U.S. patent application Ser. No. 10/708,191, in that it does not have the objective of keeping the analysis liquid (or collection liquid) from touching any surface in order to eliminate any possibility of cross contamination between samples. That is, the present application assumes that neither the particles 124, nor any parts of the particles 124, stick to the OCLT 412, the effluent pump 460, or the effluent tube 462 sufficiently to cause a problem for the characterization of the particles 124, for example, by attaching temporarily to any of these structures and then coming off later and being interpreted as coming from a later sample, or by building up inside any of these structures so much that they block the flow of the EVLC 456 through them. To help keep the particles 124 from interacting with the surface of the OCLT 412, or the effluent tube 462, the insides of these structures may be coated with whatever material, such as Teflon, or treated with whatever chemical process that may be useful in reducing the attraction of the particles 124 to them. The coating or treatment may be chosen to be the same as that used in the instrument that accepts the EVCL 456 after it exits from the ALC 100. Because the present application does not have the objective of keeping the EVCL 456 from touching any surface until after the first analysis is completed, it differs from Hill, U.S. patent application Ser. No. 10/708,191, in that there is no need for a charged droplet generator, or for a second linear quadrupole to levitate the droplets during the analysis.

The present invention differs from Lin and Hill (U.S. patent application Ser. No. 10/816,579) in that it: (a) uses a linear quadrupole to focus the particles, (b) is not restricted to collecting the particles into an analysis liquid, and (c) does not require ejecting the analysis liquid toward a collection vessel if further analysis is desired, and provides, in some embodiments, a OCLT 412 through which the particles can be drawn out from the gas-tight container 140.

In some embodiments, in which the CLP 414 pumps more CL 480 into the VCLO 450 to keep it relatively large as water evaporates from the VCLO 450, the humidity and temperature of the gas 120 in the ALC 100 are measured by a humidity-temperature sensor 180 so that the measured humidity and temperature can be used, with the help of look up tables, to determine the amount of water, in cases where the main solvent in the CL 480 is water, or other solvent, that will evaporate from the VCLO 450 during the measurement, so that: (i) the amount of additional CL 480 the CLP 414 needs to pump into the VCLO 450 can be determined and pumped into the VCLO 450 in order to keep the VCLO 450 large during the time when the particles 124 are drawn to and collide with the VCLO 450 so that more particles can be drawn to the VCLO 450, and to determine when the CLP 414 should stop pumping CL 480 into the VCLO 450, and (ii) in cases where there are solutes in the CL 480 and the concentrations of these solutes must be in some required range, the CL 480 can be prepared with the required concentrations of solutes to compensate for any water that evaporates from the VCLO 450 during the time to collect the particles 124, so that these concentrations of solutes in the VCLO 450 are kept in the required range.

In a preferred embodiment, the charger 250 employs the alternating-current corona charging method in order to impart more charge per particle 124 with fewer particles 124 lost, as described by M. Lakowski, "Unipolar charging of aerosol particles in alternating electric field," Journal of Electrostatics, 51–52, 225–231 (2001), especially FIG. 2 on page 228 of that paper and the description of the apparatus on pp. 227 and 228, both of which are herein incorporated by reference. An advantage, for some applications, of imparting more charge per particle 124, is that: (a) these particles 124 can then be focused by the LQ 500 with a lower voltage applied to the LQ 500, or with a lower frequency of the voltage applied to the LQ 500, or, (b) for some given applied voltage and LQ 500, a higher fraction of the particles 124, may be focused so that they combine with the EVCL 456. Further description of such a unipolar charger is described in M. Lakowski, A. Jaworek, and A. Krupa, "Current-voltage characteristics of alternating electric field charger," Journal of Electrostatics, 58, 77–89 (2003), herein incorporated by reference.

In another embodiment, particles 124 are charged using a commercially available ionizer, such as the AS 150MM supplied by Wein Products, Inc., Los Angeles, Calif., which was used by G. Mainelis, K. Willeke, A. Adhikari, T. Reponen, and S. A. Grinshpun, "Design and Collection Efficiency of a New Electrostatic Precipitator for Bioaerosol Collection," Aerosol Science and Technology, 36, 1073–1085 (2002), especially pp. 1074–1075, herein incorporated by reference. In one embodiment the charger 250 is of the corona-discharge type as described by R. Vehring, C. L. Aardahl, G. Schweiger and E. J. Davis, "The characterization of fine particles originating from an uncharged aerosol: size dependence and detection limits for Raman analysis," Journal of Aerosol Science, 29, 1045–1061 (1998), especially pp. 1048–1050, and p. 1057, and by C. L. Aardahl, et al., Electrodynamic trapping of aerocolloidal particles: experimental and theoretical trapping limits," Journal of Colloid and Interface Science, 192, 228–237 (1997), both herein incorporated by reference, especially pp. 231–233 of the second reference.

Figure 1A:
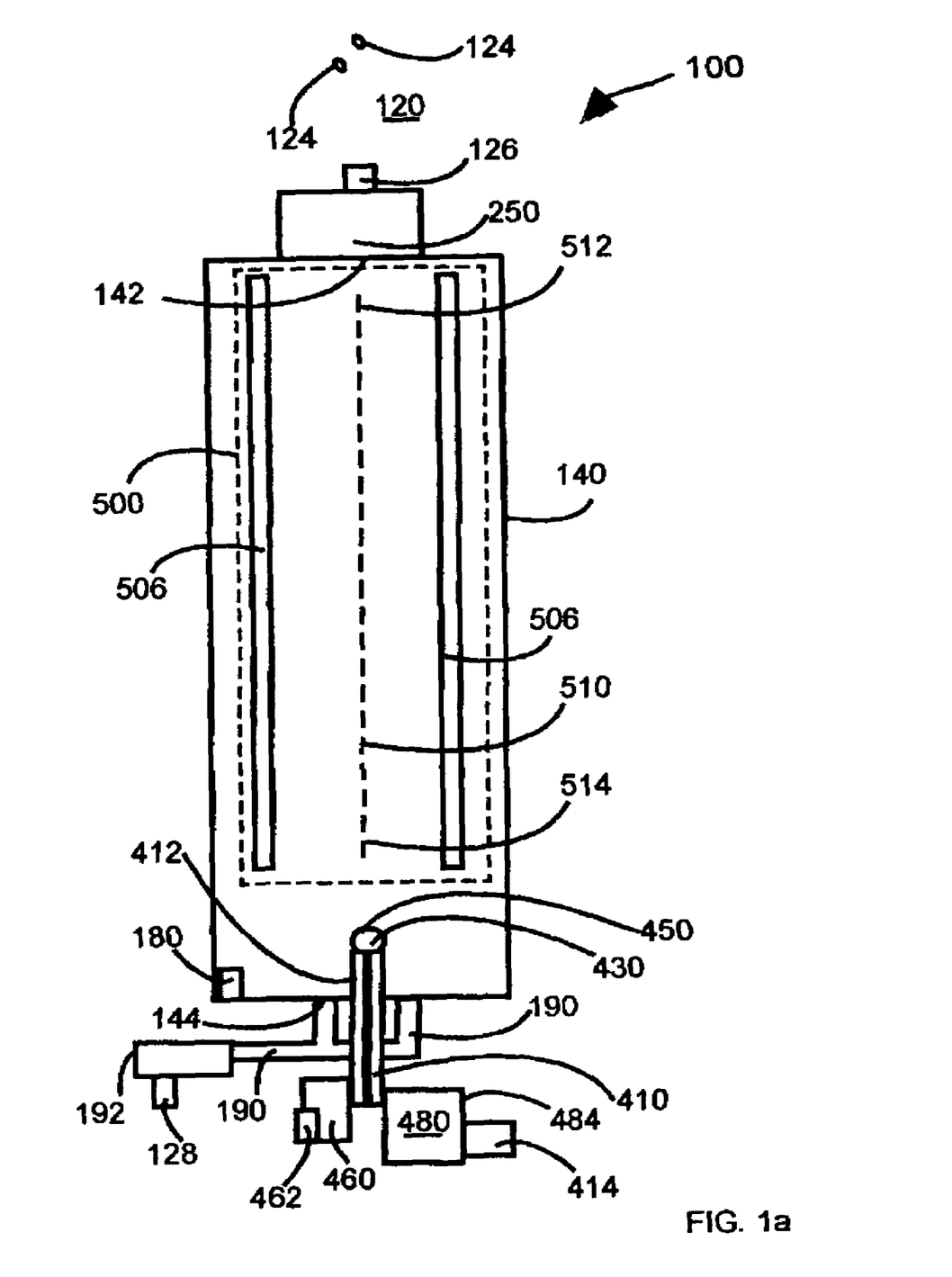
Figure 1B:
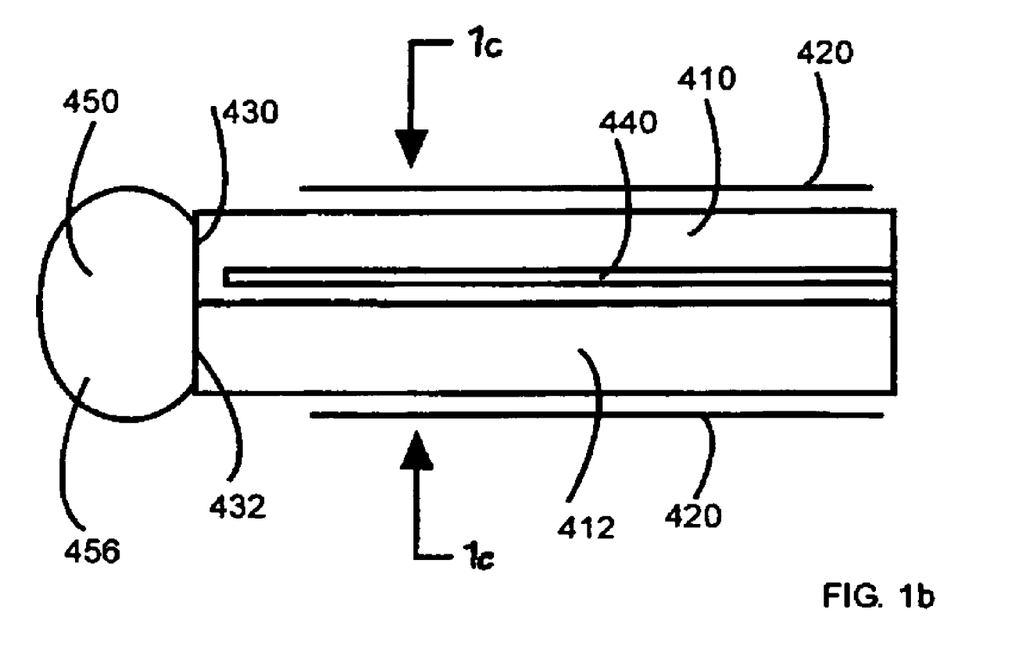
Figure 1C:
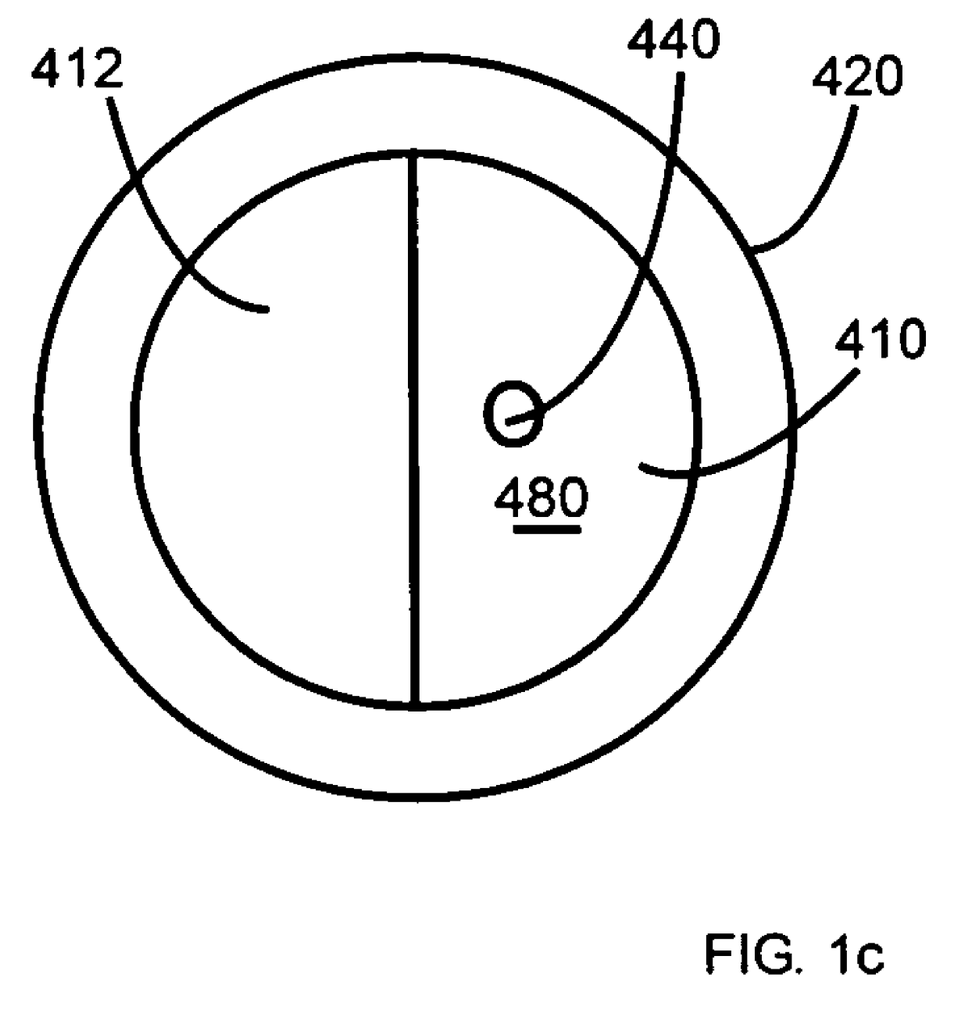

In another exemplar, the ALC 100 is as in FIG. 1a, but it does not have the charger 250. Atmospheric particles typically carry only a small charge, so the collection efficiency of this exemplar is lower than the embodiments that include a charger 250. However, airborne microorganisms tend to carry a negative charge, at least relatively soon after aerosolization (see G. Mainelis, K. Willeke, P. Baron, S. A. Grinshpun, and D. Reponen, "Induction Charging and Electrostatic Classification of Micrometer-Size Particles for Investigating the Electrobiological Properties of Airborne Microorganisms," Aerosol Science and Technology, 36, 479–491 (2002), herein incorporated by reference). Mainelis et al., show that aerosolized sodium chloride tends to carry relatively little intrinsic charge (FIGS. 6, 7a and 8a of Mainelis et al.), but that aerosolized bacteria tend to carry many times as many negative charges (FIGS. 5, 7a and 8a of Mainelis et al.).

We surmise, then, that intentionally aerosolized biological particles may be dispersed in such a way that they carry more charge than typical atmospheric aerosols and so, when the ALC 100 is used without any charger 250, or with no voltage applied to the charger 250, the fraction of particles 124 that collide with the VCLO 450 that are biological may be relatively large, especially when the VCLO 450 is given a positive charge, and especially when the voltage on the LQ 500 is relatively large. However, most particles would still carry less charge than they do after passing through a charger, and so the efficiency of collection for particles 124 that pass through an efficient charger 250 will tend to be significantly larger.

Although the collection of particles 124 that are biological has been emphasized here, the application of this invention is not restricted to collection of particles 124 that are biological, nor is it restricted to atmospheric particles.

In some embodiments of the ALC 100, for applications in which the particles 124 of interest already have a substantial charge, then it may not be desired to use the charger 250. The charges may have been imparted to the particles 124 either intentionally or non-intentionally, because of the way the particles 124 were generated, or because they were illuminated with ultraviolet light, or because of frictional forces that generated triboelectric charges, or for other reasons. In some applications the goal may be to collect particles that happen to have charge to mass ratios within a certain range.

Because the rate at which particles 124 become charged depends upon the composition of the particles 124, and because the stability of the charged particles 124 in the LQ 500 depends upon the charge, mass, and mobility of the particle 124 and on the voltage, including frequency, applied to the LO 500, the APC 100 can be designed to preferentially collect particles 124 having certain compositions and sizes. In cases where it is desired to collect a large range of sizes of particles 124 and it is not possible or not desirable to have the charger 250 impart the amount of charge to particles 124 so that all of the desired particles 124 can be collected using one voltage and frequency on the LQ 500, then in one embodiment that could achieve the objective of collecting the desired particles 124, the voltage on the LQ 500 is first set at one voltage and the particles 124 are collected, and then the voltage on the LQ 500 is cycled to a different value, and particles 124 having different characteristics are collected.

The term vacuum pump 192 in this patent application indicates a means to generate a vacuum; it includes both fans and blowers, in addition to other types of vacuum pumps such as rotary-vane pumps, or gas diaphragm pumps.

In another embodiment the ICLT 410 is conducting and is given a positive charge, so that no separate wire electrode 440 is required. In another embodiment a wire electrode 440 is positioned to be in contact with the VCLO 450 and is used to set the voltage of it; this wire electrode 440 may or may not be in contact with the ICLT 410 or the OCLT 412. The distance that the end of the electrode can be from VCLO 450 is larger in cases where the conductivity of the CL 480 is large.

In another embodiment, the VCLO 450 is given a negative charge, and the particles 124 are given a positive charge by the charger 250 so they are drawn to the VCLO 450.

In another embodiment, there is no wire electrode 440 and the VCLO 450 is uncharged and so the forces driving the particles 124 to collide with the VCLO 450 are inertial and gravitational forces. Note that in the work described by K. C. Ng, J. V. Ford, S. C. Jacobson, J. M. Ramsey, and M. D. Barnes, "Polymer microparticle arrays from electrodynamically focused microdroplet streams," Review of Scientific Instruments, 71, 2497–2499 (2000), that has been incorporated by reference, the particles were not drawn to a particular spot on the surface by any fields coming from the surface, but were first focused by the linear quadrupole, and then after these particles exited the linear quadrupole they continued on their trajectory and impacted on the flat surface underneath the quadrupole.

In another embodiment multiple stages of LQ 500 are used in order to increase the volume of the gas entering the APC 100 that can be focused to within a very small distance of the LQ axis 510, and so to increase the volume of gas from which particles 124 can be collected.

Aerosol concentrators that concentrate the particles in air have been used in combination with a variety of aerosol detectors and collectors to concentrate the particles in air before they enter the detector or collector. Examples of commercially available virtural impactor concentrators are the MicroVIC sold by Mesosystems, from Albuquerque, N. Mex., and the XMX sold by Dycor Technologies, Ltd., Edmonton, Canada.

For some applications, it may be useful to employ such an aerosol concentrator in combination with the ALC 100, so that more particle can be collected from gas 120 for a given concentration of particles 124 in the gas 120.

Figure 2:
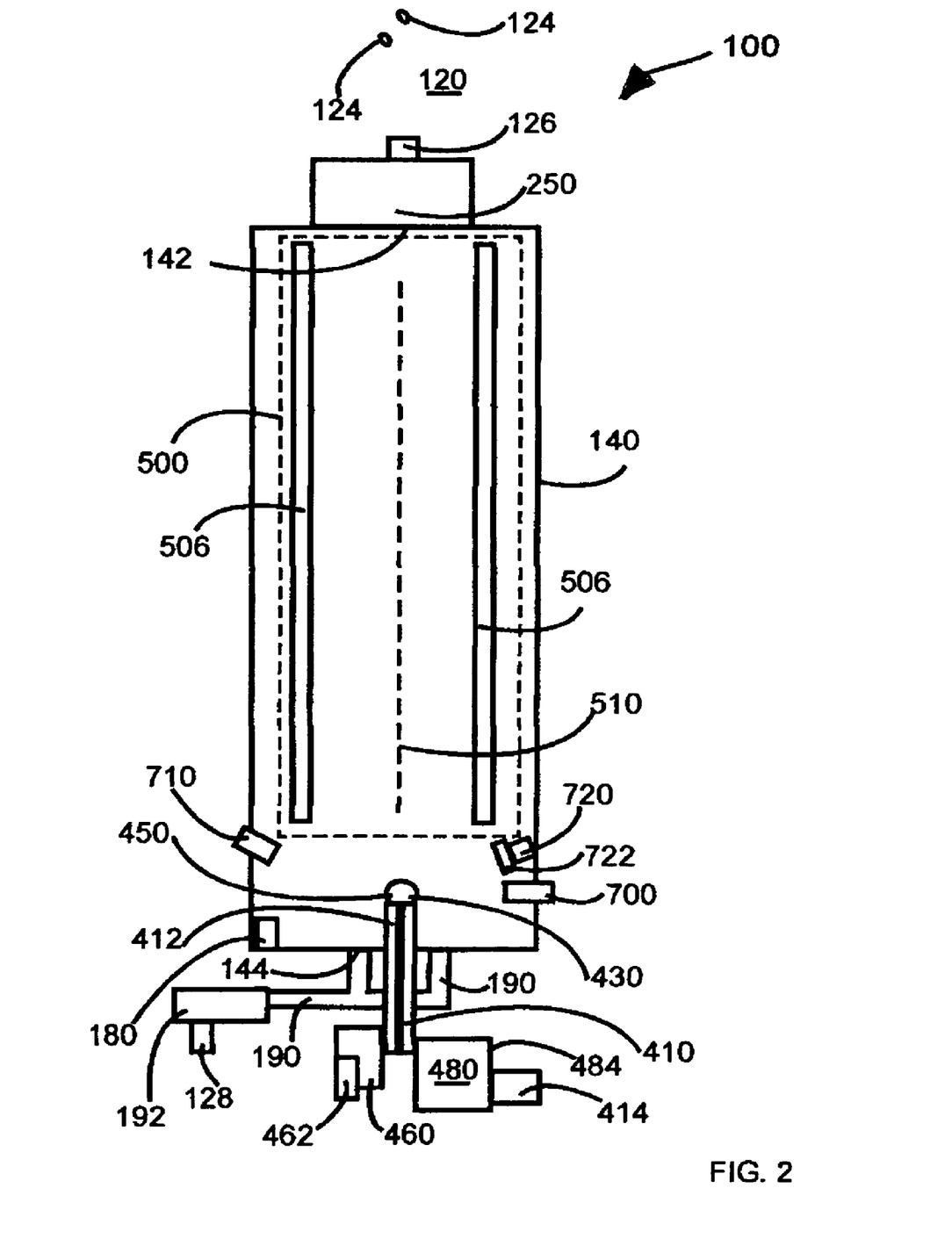

Another embodiment of the ACL 100 is shown in FIG. 2. The illustration is similar to that shown in FIG. 1a, but includes additional features. One is the use of a laser diode 700 and a photodetector 710 to monitor the VCLO 450 by light scattering. The light from the laser diode 700 illuminates the VCLO 450 and the light scattered by the VCLO 450 is detected by the photodetector 710. The signal from the photodetector 710 is then used to determine when the CLP 414 needs to pump more CL 480 into the VCLO 450. A third additional feature illustrated in FIG. 2 is the fluorescence photodetector 720 and optical filter 722 which is positioned to detect any change in fluorescence of the VCLO 450 as the particles 124 combine with it. For this embodiment, the laser diode 700 illuminates the VCLO 450 with light having a wavelength such that it can excite fluorescence in the CL 480 when the particles 124 that combine with it have certain constituents of interest. A discussion of how the CL 480 can be chosen, or designed, to fluoresce when it comes in contact with particles 124 of the type that are of interest is in Hill, U.S. patent application Ser. No. 10/708,191, already incorporated by reference.

In FIG. 1a, and FIG. 2 the VCLO 450 is centered on the extension of the second end of the LQ axis 514, and the flow of the gas 120 exiting from the LQ 500 is also centered on the extension of the second end of the LQ 514. However, that arrangement is not always necessary. Once particles 124 that have been focused to the LQ axis 510 leave the LQ 500, they will tend to continue to move with the flow of the gas 120. If, the flow of the gas 120 diverges from its motion parallel to the LQ axis 510 after it exits from the LQ, but still remains laminar, the focused particles will also tend to diverge away from the extension of the second end of the LQ axis 514. In such cases, either the direction of the flow of the gas 120 can be adjusted, for example by adjusting the flow through the gas outlets 144, or the VCLO 450 can be moved to the streamline of the gas 120 along which the concentrated particles 124 flow. For either type of adjustment, calibration particles, a laser beam to illuminate the calibration particles, and for some particles a sensitive camera to photograph the particles may be useful. For some applications it may be desirable to have the flow of the gas 120 away from the extension of the second end of the LQ axis 514, for example in cases in which the direction of the flow of the gas 124 is intentionally adjusted from one stable trajectory to another, in cases, for example where multiple VCLO 450 are employed, possibly where each VCLO 450 contains different composition of CL 480.

In many particle-sampling devices a sheath flow surrounding the flow of the gas that carries the particles of interest is used to keep the gas flow and the particles in it from spreading out further than it otherwise would. A means to generate a sheath flow around the flow of the gas 120 carrying the charged particles 124 is useful for certain embodiments of the ALC 100, where the usefulness depends upon such parameters as the gas 120 flow rates desired, the type of charger 250 used, and limitations on LQ 500 size.

For some applications it is useful to know the numbers and sizes of the particles 124 in the gas 120 that is drawn into the ALC 100, in order, for example, to estimate the concentrations of certain types of materials in particles 124, for example on a per mass basis. For such applications, aerosol particle counters of one of the common types commercially available can be combined with the ALC 100 to make these measurements.

In the detailed descriptions of the ALC 100 given above the volume of the collection liquid 480 that is exposed to the particles 124 that were concentrated by the LQ 500 to become the EVCL 456 is always held at an opening at the end of a ICLT 410 or a OCLT 412, because our primary interest is in providing the EVCL 456 to instrumentation that will take the EVCL 456 into a tube. However, many variations of the basic invention can be envisioned. We do not wish to state them all in detail, but simply to mention some possible ones. For example, for some applications it may be desired that the EVCL 456 be delivered on a surface to the instrumentation that does the further analysis. In such cases, the volume of collection liquid 480 could be placed on a surface, by any of a number of means, and that surface could be positioned so that the particles 124 focused to the LQ axis 510 tend to impact upon that volume of collection liquid 480. This surface could be a flat surface that may contain an array of droplets and is stepped from one position to the next, or it may be a small diameter rod, or it may be a belt.

Although various preferred embodiments of the present invention have been described herein in detail to provide for complete and clear disclosure, it will be appreciated by those skilled in the art that variations may be made thereto without departing from the spirit of the invention or the scope of the appended claims.

We claim:

1. An Aerosol-into-liquid collector (ALC) for collecting any particles found in a gas comprising:
   (a) an aerosol particle handling subsystem further consisting of:
   (i) a substantially gas-tight container,
   (ii) a gas inlet,
   (iii) a linear quadrupole (LQ) consisting of four rods situated symmetrically around and parallel to an LQ axis having a first end and a second end, where said linear quadrupole is positioned inside the gas-tight container such that the gas inlet is centered on an extension of the first end of the LQ axis,
   (iv) a vacuum pump,
   (v) and at least one gas outlet that has a gas-tight connection to the vacuum pump, where the gas inlet, the LQ, and the gas outlets are positioned such that: when the vacuum pump generates a vacuum in the gas outlets, the gas that is drawn into the gas-tight container flows into the LQ, where the flow of gas into the LQ is centered on the LQ axis, and where at least some of the particles that have a combination of charge, mass, and mobility that is stable in the LQ, are focused toward the LQ axis, and are then drawn from the LQ substantially near the LQ axis so that the concentrated particles can be collected relatively efficiently;
   (b) a collection liquid (CL);
   (c) a means to generate and hold a volume of the collection liquid (VCL) within the path taken by particles that were focused by the LQ to positions near the LQ axis, so that these particles tend to combine with the VCL and so that the VCL that is exposed to the gas and particles becomes an exposed volume of collection liquid (EVCL);
   (d) a means to move the EVCL out of the gas-tight container through an output liquid port in the gas-tight container so that this EVCL can be analyzed by whatever instrumentation is connected to this output port.

2. The ALC of claim 1 wherein the ALC further includes a charger which has a gas inlet and which is connected with a gas-tight connection to the gas inlet of the gas tight container, and which imparts a charge to particles drawn through it.

3. The ALC of claim 2 wherein the charger generates a corona discharge.

4. The ALC of claim 3 wherein the charger is a unipolar, alternating-current, corona charger.

5. The ALC of claim 1 wherein the means to generate and hold a volume of the collection liquid further includes an incoming section of collection liquid tube that has an opening at its distal end, where the VCL is held in order to be exposed to the gas and any particles contained in the gas.

6. The ALC of claim 5 wherein the means to generate and hold a volume of the collection liquid further includes a collection liquid pump which pumps the collection liquid through the incoming collection liquid tube toward the opening at the distal end of the incoming collection liquid tube so that a VCL is positioned and held at the opening so that it can be exposed to the gas and any particles contained in the gas.

7. The ALC of claim 6 wherein the means to generate and hold a volume of the collection liquid further includes a collection liquid reservoir from which the collection liquid pump draws the collection liquid that it pushes into the incoming collection liquid tube.

8. The ALC of claim 1 wherein the means to move the exposed volume of the collection liquid through an output liquid port includes an outgoing collection liquid tube that is positioned between the region in which the VCL is held and the output liquid port.

9. The ALC of claim 1 wherein the ALC further includes a means to impart a charge to the VCL and EVCL so that electrostatic forces between the charged VCL and oppositely charged particles in the gas increase the fraction of particles that collide with the VCL and EVCL.

10. The ALC of claim 9 wherein the ALC further includes a shield electrode around the incoming collection liquid tube and outgoing collection liquid tube, where this shield electrode is given a potential opposite that of the collection liquid.

11. The ALC of claim 1 wherein said ALC further includes a temperature sensor and a humidity sensor, so that the measured temperature and humidity of the gas in the gas-tight container can be used to determine the rates and times at which the effluent pump and the collection liquid pump move the collection liquid and the EVCL toward or away from the VCL.

12. The ALC of claim 1 further including an aerosol particle counter to measure the concentration of, and sizes of, particles in the gas so that the numbers and sizes of particles that combine with the VCL can be approximately determined by using calibration data.

13. The ALC of claim 1 further including a laser diode to illuminate the VCL and a photodetector to measure the light scattered by the VCL so that this measurement of the scattered light can be used to determine if the size of the VCL is becoming smaller than desired, and so the collection liquid pump can be directed to pump more collection liquid into the VCL being held at a location where focused particles from the gas tend to combine with it.

14. The ALC of claim 1 further including a laser diode to illuminate the VCL and a filter to block the scattered light, and a photodetector to measure the fluorescence emitted from VCL when it has combined with particles so that this measurement of the fluorescence can be used to determine characteristics of the particle, depending upon the collection liquid used.

15. The ALC of claim 1 wherein said VCL is centered on the extension of the second end of the LQ axis, and in which the center of the gas flow after it exits the LQ remains near this extension of the second end of the LQ axis.

* * * * *